(12) United States Patent
Rhee et al.

(10) Patent No.: US 8,313,905 B2
(45) Date of Patent: Nov. 20, 2012

(54) DETECTION OLIGOMER AND METHOD FOR CONTROLLING QUALITY OF BIOCHIP USING DETECTION OLIGOMER

(75) Inventors: Joo-Won Rhee, Daejeon (KR); Byung-chul Kim, Suwon-si (KR); Sun-Ok Jung, Suwon-si (KR); Seung-Hei Cho, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 764 days.

(21) Appl. No.: 12/358,530

(22) Filed: Jan. 23, 2009

(65) Prior Publication Data

US 2009/0239770 A1    Sep. 24, 2009

(30) Foreign Application Priority Data

Jan. 24, 2008   (KR) .................................. 2008-7675

(51) Int. Cl.
*C12Q 1/68* (2006.01)
*C12P 19/34* (2006.01)
*C07H 21/02* (2006.01)

(52) U.S. Cl. ..................... 435/6.1; 435/91.2; 536/23.1

(58) Field of Classification Search ........................ None
See application file for complete search history.

(56) References Cited

U.S. PATENT DOCUMENTS

| | | | |
|---|---|---|---|
| 5,215,899 A | 6/1993 | Dattagupta | |
| 5,925,517 A | 7/1999 | Tyagi et al. | |
| 6,114,121 A | 9/2000 | Fujiwara et al. | |
| 6,383,754 B1 | 5/2002 | Kaufman et al. | |
| 6,403,319 B1 | 6/2002 | Lizardi et al. | |
| 6,686,150 B1 | 2/2004 | Blackburn et al. | |
| 6,861,222 B2 | 3/2005 | Ward et al. | |
| 2005/0074781 A1 | 4/2005 | von Schroeder et al. | |
| 2007/0111226 A1 * | 5/2007 | Tan et al. ........................ | 435/6 |
| 2007/0172845 A1 | 7/2007 | Wang | |

FOREIGN PATENT DOCUMENTS

| | | |
|---|---|---|
| EP | 0427073 | 10/1990 |
| WO | 99/11813 | 3/1999 |
| WO | 01/12856 | 2/2001 |
| WO | 01/25485 | 4/2001 |
| WO | 2004050916 | 6/2004 |
| WO | 2005007815 | 1/2005 |
| WO | 2005/030987 | 4/2005 |
| WO | 2007025281 | 3/2007 |

OTHER PUBLICATIONS

Broude N.E. et al. Nucl. Acids Res. (2001) 29 (19): e92 pp. 1-11.*
Yao G. et al. Analytical Biochemistry 331 (2004) 216-223.*
Riccelli et al., Nucleic Acids Research, vol. 29, 2001, 'Hybridization of single-stranded DNA targets to immobilised complementary DNA probes: comparison of hairpin versus linear capture probes', pp. 996-1004 see the whole document.
United Kingdom Search Report issued Apr. 28, 2009 in GB 0901054.7.
British Office Action issued Feb. 2, 2012 in British Application No. 0901054.7.

* cited by examiner

*Primary Examiner* — Stephen Kapushoc
(74) *Attorney, Agent, or Firm* — Stanzione & Kim, LLP

(57) ABSTRACT

A detection oligomer and method for controlling the quality of a biochip using the detection oligomer are provided. The detection oligomer includes a template having a first and second end and having a sequence that is complementary to a specific sequence of an oligomer, and a hairpin connected to the first end of the template.

11 Claims, 10 Drawing Sheets

SEQUENCE LISTING

```
<160> NUMBER OF SEQ ID NOS: 3

<210> SEQ ID NO 1
<211> LENGTH: 54
<212> TYPE: DNA
<213> ORGANISM: Artificial Sequence
<220> FEATURE:
```

```
<223> OTHER INFORMATION: Synthetic

<400> SEQUENCE: 1
ttccagggcg cgagttgata gctggcttaa gaggcgtcta gtacgcctct taag        54

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ccagctatca actcgcgccc tggaa                                        25

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cagctatcaa ctcgcgccct ggaa                                         24
```

US 8,313,905 B2

DETECTION OLIGOMER AND METHOD FOR CONTROLLING QUALITY OF BIOCHIP USING DETECTION OLIGOMER

CROSS-REFERENCE TO RELATED APPLICATIONS

This application claims the benefit under 35 U.S.C. §119 (a) from Korean Patent Application No. 10-2008-0007675 filed on Jan. 24, 2008 in the Korean Intellectual Property Office, the disclosure of which is incorporated herein in its entirety by reference.

BACKGROUND OF THE INVENTION

1. Field of the Invention

The present general inventive concept relates to a detection oligomer and method for controlling the quality of a biochip using the detection oligomer, and more particularly, to a detection oligomer containing a hairpin structure and a method for controlling the quality of a biochip using the detection oligomer.

2. Description of the Related Art

A biochip is used to analyze the constituents of biological samples by monitoring a reaction between the biological samples and a matrix of probes immobilized on a chip substrate, when the biological samples are introduced to the probes. Each cell in a biochip has different probes immobilized on a surface thereof, thereby allowing detection of various data.

As an amount of data to be analyzed increases, various kinds of probes that can hybridize with bio-molecules need to be coupled and immobilized onto the biochip. The use of the various kinds of probes being coupled and bound to a biochip heightens an importance of quality control (QC) of biochips that involve determining whether or not a probe having a desired base sequence is bound to the biochip.

SUMMARY OF THE INVENTION

The present general inventive concept provides a detection oligomer capable of efficiently controlling the quality of a biochip.

The present general inventive concept also provides a method of efficiently controlling the quality of a biochip.

The above and other objects of the present general inventive concept will be described in or be apparent from the following description of the exemplary embodiments.

Additional aspects and/or utilities of the present general inventive concept will be set forth in part in the description which follows and, in part, will be obvious from the description, or may be learned by practice of the general inventive concept.

The foregoing and/or other utilities of the present general inventive concept may also be achieved by providing a detection oligomer including a template having a sequence that is complementary to a specific sequence of an oligomer, and a hairpin connected to one end of the template.

The foregoing and/or other utilities of the present general inventive concept may also be achieved by providing a printing a detection oligomer including a first single-stranded oligomer having a sequence complementary to an oligomer having a specific sequence, and a second single-stranded oligomer connected to one end of the first oligomer and having a sequence that can form a hairpin structure.

The foregoing and/or other utilities of the present general inventive concept may also be achieved by providing a method of controlling the quality of a biochip, the method including providing a biochip including a plurality of probes, each of which has one end coupled to an immobilization layer, wherein the plurality of probes include a first probe having a desired number of monomers and a second probe having an undesired number of monomers, hybridizing a QC (Quality Control) probe to the first and second probes coupled to the immobilization layer, connecting the QC probe with the first probe, and removing the hybridization coupling between each of the first and second probes and the QC probe, wherein the QC probe includes a template having a sequence complementary to a base sequence of the first probe and a hairpin connected to one end of the template.

The foregoing and/or other utilities of the present general inventive concept may also be achieved by providing a detection monomer which includes a template having a first and second end and having a sequence that is complementary to a specific sequence of a monomer, and a hairpin connected to the first end of the template.

The foregoing and/or other utilities of the present general inventive concept may also be achieved by providing a method of forming a detection monomer, the method includes forming a template having a first and second end and having a sequence that is complementary to a sequence of a monomer and forming a hairpin connected to the first end of the template.

The foregoing and/or other utilities of the present general inventive concept may also be achieved by providing a biochip which includes a detection monomer having a template with a first and second end and having a sequence that is complementary to a predetermined sequence of a monomer and a hairpin connected to the first end of the template.

BRIEF DESCRIPTION OF THE DRAWINGS

The above and/or other aspects and utilities of the present general inventive concept will become more apparent by describing in detail exemplary embodiments thereof with reference to the attached drawings in which.

The above and/or other aspects and utilities of the present general inventive concept will become more apparent by describing in detail exemplary embodiments thereof with reference to the attached drawings in which.

DETAILED DESCRIPTION OF THE PREFERRED EMBODIMENTS

Figure 1:
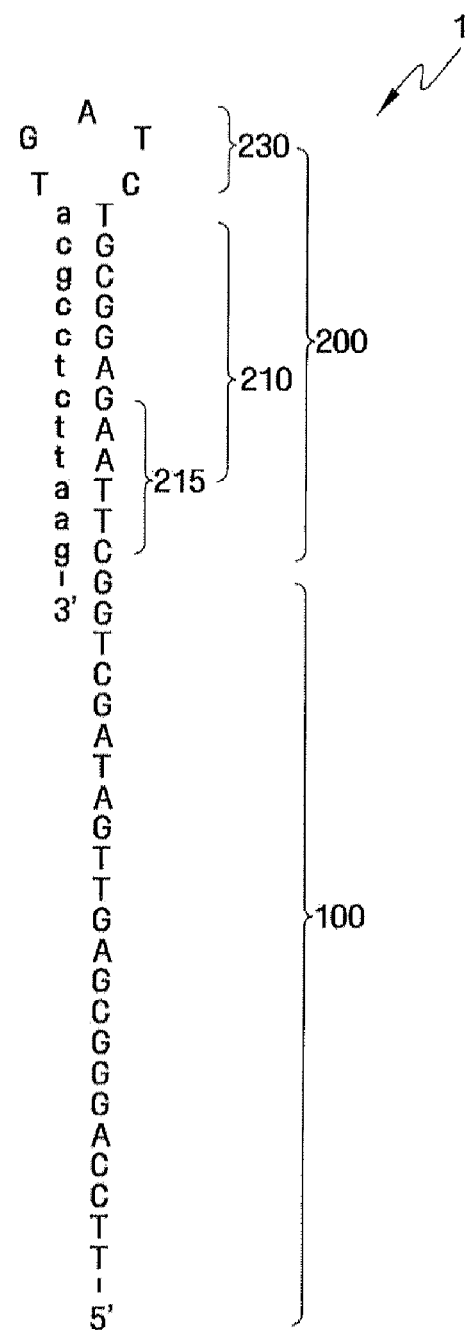
FIG. 1 illustrates a detection oligomer according to an exemplary embodiment of the present general inventive concept.

Utilities and/or features of the present general inventive concept and methods of accomplishing the same may be understood more readily by reference to the following detailed description of exemplary embodiments and the accompanying drawings. The present general inventive concept may, however, be embodied in many different forms and should not be construed as being limited to the exemplary embodiments set forth herein. Rather, these exemplary embodiments are provided so that this disclosure will be thorough and complete and will fully convey the concept of the present general inventive concept to those skilled in the art, and the present general inventive concept will only be defined by the appended claims.

Accordingly, in some specific exemplary embodiments, well known processing steps, structures, or methods have not been described in detail in order to avoid obscuring the present general inventive concept.

It is noted that the use of any and all examples, or exemplary terms provided herein is intended merely to better illuminate the present general inventive concept and is not a limitation on the scope of the present general inventive concept unless otherwise specified. As used herein, the singular forms "a," "an" and "the" are intended to include the plural forms as well, unless the context clearly indicates otherwise. It will be further understood that the terms "comprises" and/or "comprising" when used in this specification, specify the presence of stated features, regions, integers, steps, operations, elements, and/or components, but do not preclude the presence or addition of one or more other features, regions, integers, steps, operations, elements, components, and/or groups thereof. As used herein, the term "and/or" includes any and all combinations of one or more of the associated listed items. Like numbers refer to like elements throughout.

The present general inventive concept will be described with reference to perspective views, cross-sectional views, and/or plan views, in which exemplary embodiments of the present general inventive concept are shown. Thus, the profile of an exemplary view may be modified according to manufacturing techniques and/or allowances. That is, the exemplary embodiments of the invention are not intended to limit the scope of the present general inventive concept but cover all changes and modifications that may be caused due to a change in manufacturing process. Thus, regions shown in the drawings are illustrated in schematic form and the shapes of the regions are simplified or exaggerated by way of illustration and not as a limitation.

FIG. 1 illustrates a detection oligomer according to an exemplary embodiment of the present general inventive concept.

For convenience of explanation, while a detection oligomer used hereinafter includes a template having a free 5'-terminus and a hairpin which is not coupled with the template and having a 3'-terminus stem, oligomers having various other structures may also be used in the present general inventive concept. Further, while a template and a hairpin of a detection oligomer used in the present general inventive concept are described to have specific base sequences for convenience of explanation, it will be understood by those skilled in the art that the type of a target sample to be detected may vary depending on a specific sequence and hairpin structure of an oligomer. In exemplary embodiments, a portion may refer to a sub sequence of an oligomer or may refer to an entire portion of a sequence of an oligomer.

Referring to FIG. 1, a detection oligomer 1 according to an exemplary embodiment of the present general inventive concept includes a template 100 and a hairpin 200.

The template 100 has a sequence complementary to a specific sequence of an oligomer such that the detection oligomer 1 hybridizes with the oligomer having the specific sequence.

In addition, the detection oligomer 1 may hybridize with a "Hybridization" is a technique for binding bases having complementary sequences together by a formation of hydrogen bonds therebetween. In exemplary embodiments, the oligomer having the specific sequence may be a probe immobilized on a biochip. In this case, since the template 100 has a base sequence that is complementary to a base sequence of the probe, hybridization may occur between the template 100 and the probe.

Biochips according to some exemplary embodiments of the present general inventive concept analyze biomolecules contained in biological samples and are used in gene expression profiling; genotyping through detection of mutation or polymorphism such as Single-Nucleotide Polymorphism (SNP), protein or peptide assays; potential drug screening; development and preparation of novel drugs, etc. However, the present general inventive concept is not limited thereto. Biochips employ appropriate probes according to the type of biological sample which is to be analyzed. Examples of probes useful for biosensors include a DNA probe, a protein probe such as an enzyme, an antibody/antigen or a bacteriorhodopsin, a bacterial probe, a neuron probe, and so on. The biochip may also include a "lab-on-a-chip" which integrates pre-treating, biochemical reacting, detecting, and data analyzing functions in order to achieve an auto-analysis function. In exemplary embodiments, the biochip includes an array of biochemically active substances or oligomer probes arranged on a plastic, glass, or silicon substrate. A biosensor fabricated in the form of a chip may also be referred to as a biochip. For example, according to the type of probe used, the biosensor may be referred to as a DNA chip, a protein chip, a cellular chip, a neuron chip, and so on.

Biochips according to some exemplary embodiments of the present general inventive concept may comprise oligomer probes. As used herein, the term "oligomer" is a low-molecular weight polymer molecule consisting of two or more covalently bound monomers. Oligomers have a molecular weight of about 1,000 or less. In exemplary embodiments, the oligomer may include about 2-500 monomers. In other exemplary embodiments, the oligomer may include about 5-300 monomers. In yet other exemplary embodiments, the oligomer may include about 5-100 monomers. However, the present general inventive concept is not limited thereto.

In exemplary embodiments, the monomers may be nucleosides, nucleotides, amino acids, peptides, etc., depending on the type of probes. As used herein, the terms "nucleosides" and "nucleotides" include not only known purine and pyrimidine bases, but may also include methylated purines or pyrimidines, acylated purines or pyrimidines, etc. Furthermore, the "nucleosides" and "nucleotides" include not only known (deoxy)ribose, but may also include a modified sugar which contains a substitution of a halogen atom or an aliphatic group for at least one hydroxyl group or is functionalized with ether, amine, or the like. As used herein, the term "amino acids" are intended to refer to not only naturally occurring, L-, D-, and nonchiral amino acids, but may also include modified amino acids, amino acid analogs, etc. As used herein, the term "peptides" refer to compounds produced by an amide bond between the carboxyl group of one amino acid and the amino group of another amino acid.

The hairpin 200 is connected to a first end (3'-terminus) of the template 100 and includes a stem 210 and a loop 230. (SEQ ID NO. 1).

The stem 210 is a double-stranded region in which complementary bases hybridize to each other to form base pairs. That is, the stem 210 includes a first single strand (a base sequence in the stem 210 indicated by capital letters) coupled to the first end of the template 100 and a second single strand (a base sequence in the stem 210 indicated by lowercase letters) hybridizing to the first single strand.

In exemplary embodiments, the first single strand has a first end coupled to the loop 230 and a second end coupled to the first end of the template 100. In an exemplary embodiment, such coupling may be provided by a covalent bond. However, the present general inventive concept is not limited thereto.

In exemplary embodiments, the second single strand has a first end coupled to the loop 230 and a second end having a 3'-terminus. In an exemplary embodiment, the second single strand has a base sequence which is complementary to the base sequence of the first single strand such that the first and second single strands hybridize to each other to form a base-pair double stranded region.

The second end of the first and/or second single strand contains a sequence 215 that is specific to a particular nuclease or chemical reaction. In this case, the particular nuclease may be endonuclease or exonuclease. For instance, the second end of the first and/or second single strand may contain a palindromic sequence that is specific to a restriction endonuclease. However, the present general inventive concept is not limited thereto.

Figure 2:
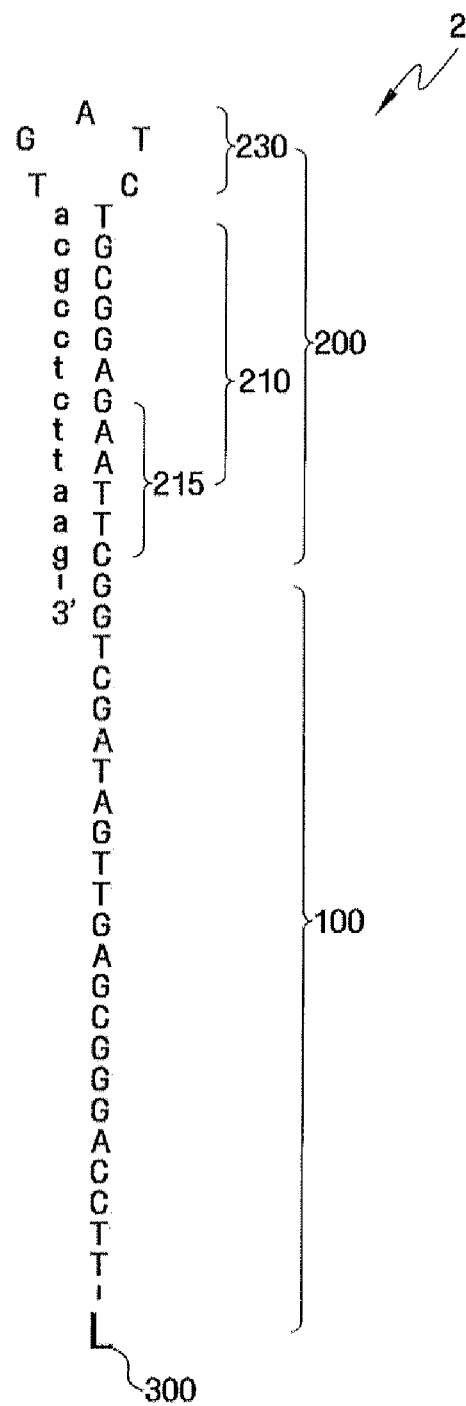
FIG. 2 illustrates a detection oligomer according to another exemplary embodiment of the present general inventive concept.

FIG. 2 illustrates a detection oligomer according to another exemplary embodiment of the present general inventive concept.

Referring to FIG. 2, unlike the detection oligomer 1 illustrated in FIG. 1, a detection oligomer 2 according to another exemplary embodiment of the present general inventive concept further includes a label 300 coupled to the template 100.

More specifically, the detection oligomer 2 further includes the label 300 coupled to the second end (5'-terminus) of the template 100. The label 300 is typically used for optical detection after hybridization between a probe immobilized on a biochip and a detection oligomer. To achieve this purpose, in exemplary embodiments, the label 300 may be made of a fluorescent or phosphorescent material selected among, but not limited to, Rhodamine 200, Calcium Green, Cyanine2, Cyanine3, Cyanine5, Magnesium Green, Tetramethylrhodamine, and Fluorescein. However, the present general inventive concept is not limited thereto.

Although not illustrated in the drawings, detection oligomers according to other exemplary embodiments of the present general inventive concept may further include labels coupled to a loop in a hairpin. In alternative exemplary embodiments, the detection oligomers may further include labels coupled to a template and a loop in a hairpin.

Figure 3:
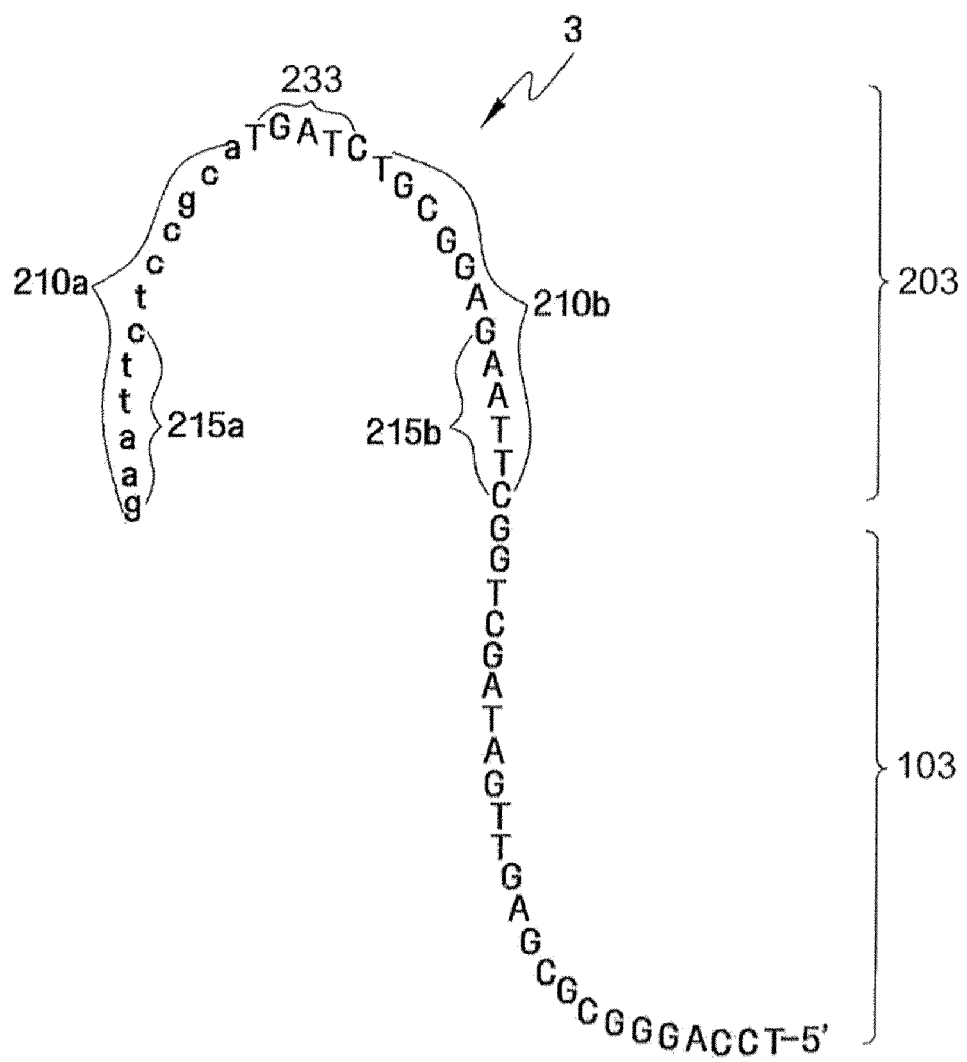
FIG. 3 illustrates a detection oligomer according to another exemplary embodiment of the present general inventive concept.

FIG. 3 illustrates a detection oligomer according to another exemplary embodiment of the present general inventive concept.

Referring to FIG. 3, a detection oligomer 3 according to another exemplary embodiment of the present general inventive concept includes a first single-stranded oligomer 103 having a sequence that is complementary to a specific sequence of an oligomer (hereinafter referred to as a "first oligomer") and a second single-stranded oligomer 203 connected to a first end or the first oligomer 103 and having a sequence that may form a hairpin structure (hereinafter referred to as a "second oligomer"). In the current exemplary embodiment, the second oligomer 203 may form a hairpin structure by an intramolecular reaction carried out according to an ambient environment such as temperature and solution. However, the present general inventive concept is not limited thereto.

In exemplary embodiments, the first oligomer 103 may have substantially similar or the same structure as the template 100 in the oligomer 1 illustrated in FIG. 1. That is, the first oligomer 103 has a sequence that is complementary to a sequence of a probe immobilized on a biochip so that it can hybridize with the probe.

The second oligomer 203 is connected to the first end (3'-terminus) of the first oligomer 103 and has a sequence that may form a hairpin structure. The base sequence of the second oligomer 203 that may form a hairpin structure may vary depending on a length and sequence of a stem in the hairpin structure which is to be formed, a length and sequence of a loop, or a temperature at which the hairpin structure is formed. In an exemplary embodiment, if the base sequence of the second oligomer 203 is designed such that free energy change during coupling at the first and second ends of the second oligomer 203 does not exceed about −20 kcal/mol, the second oligomer 203 may form a hairpin structure at room temperature.

As illustrated in FIG. 3, the second oligomer 203 is divided into first through third regions 210b, 233, and 210a that are named in order starting from a portion of the second oligomer 203 which is connected to the first end of the first oligomer 103. The first and third regions 210b and 210a of the second oligomer 203 hybridize to each other to form a stem of a hairpin while the third region 233 forms a loop of the hairpin.

The first and third regions 210b and 210a have complementary base sequences so that they hybridize to each other according to an ambient environment to form a base-pair double stranded region. That is, the first and third regions 210b and 210a of the second oligomer 203 in detection oligomer 3 according to the current exemplary embodiment may have substantially similar or the same structure as the first and second single strands of the stem 210 of the detection oligomer 1 as illustrated in FIG. 1.

Terminuses of the first and third regions 210b and 210a which are not connected to the second region 233 of the second oligomer 203 respectively contain sequences 215b and 215a that are specific to a particular nuclease or chemical reaction.

In exemplary embodiments, the second region 233 of the second oligomer 203 may have substantially similar or the same structure as the loop 230 of the hairpin in the detection oligomer 1 as illustrated in of FIG. 1.

Although not illustrated in the drawings, a detection oligomer according to another exemplary embodiment may further include a label coupled to the first oligomer 103 and/or the second oligomer 203 in the detection oligomer 3.

More specifically, if a label is coupled to the 5'-terminus of the first oligomer 103, the detection oligomer 3 may perform an intramolecular reaction according to an ambient environment to form a detection oligomer having a substantially similar or the same structure as the detection oligomer 2 illustrated in FIG. 2. Similarly, if a label is coupled to the second region 233 of the second oligomer 203, the detection oligomer 3 may perform an intramolecular reaction according to the ambient environment to form a detection oligomer in which a loop of a hairpin is tagged with the label.

A method for controlling the quality of a biochip using the detection oligomers according to exemplary embodiments of the present general inventive concept will now be described in detail.

FIGS. 4A through 4F are diagrams which illustrate a method for controlling a quality of a biochip. In exemplary embodiments, a quality control (QC) probe used in the method may be made of the detection oligomer 1 illustrated in FIG. 1.

Figure 4A:
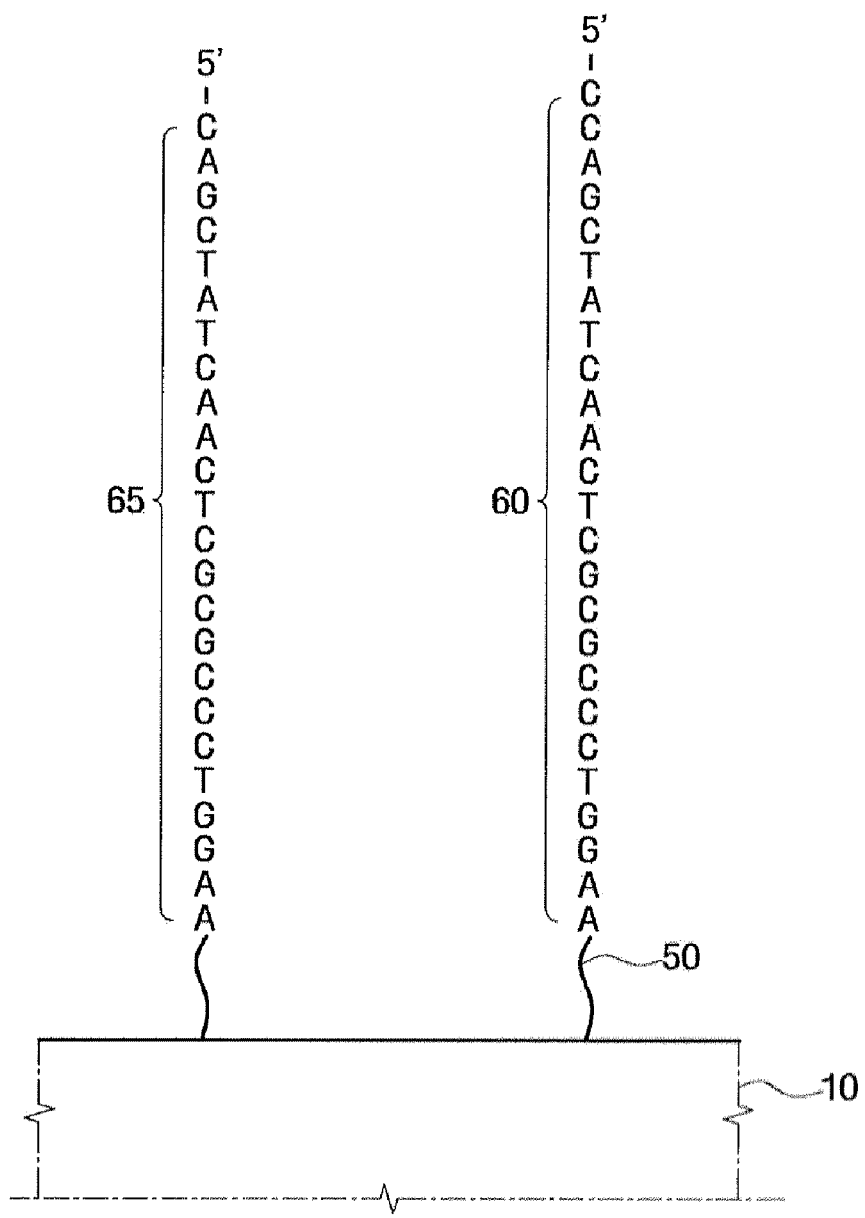
FIGS. 4A through 4E are diagrams which illustrate a method for controlling the quality of a biochip according to an exemplary embodiment of the present general inventive concept.

Referring to FIG. 4A, a biochip having a plurality of probes 60 and 65 coupled to an immobilization layer 10 is provided. The plurality of probes 60 and 65 include a first probe 60 containing a desired number of monomers which can detect bio-molecules contained in a biological sample and a second probe 65 containing an undesired number of monomers. While FIG. 4A illustrates the first probe 60 contains 25 monomers and the second probe 65 contains 24 monomers for convenience of explanation, the number of monomers in the first and second probes 60 and 65 may vary according to the type of application. That is, the present general inventive concept is not limited to 25 monomers within the first probe or 24 monomers in the second probe. Further, although FIG. 4A illustrates the 3'-terminuses of the first and second probes 60 and 65, considered herein as first ends, are respectively coupled and bound to the immobilization layer 10 and the 5'-terminuses, considered herein as second ends, thereof are free terminuses, the first and second probes 60 and 65 may have various different structures at the 5'- and 3'-terminuses, respectively.

In exemplary embodiments, the immobilization layer 10 may directly provide functional groups which may be directly or indirectly coupled with the first and second probes 60 and 65 or may be formed of a material which can provide functional groups after undergoing various surface treatments including annealing, ozone treatment, acid treatment, and alkaline treatment. Being "directly coupled" means that the immobilization layer 10 is coupled with the first and second probes 60 and 65 without any intermediate medium disposed therebetween. Being "indirectly coupled" means that the immobilization layer 10 is coupled with the first and second probes 60 and 65 via a linker 50.

The linker 50 contains functional groups (e.g., SiOH) with higher coupling reactivity than functional groups in the immobilization layer 10 and may be formed of a material that is sufficiently long in order to allow free interactions with a biological sample. In exemplary embodiments, the formation of the linker 50 may be omitted if necessary.

In exemplary embodiments, a method of fabricating the biochip with the probes 60 and 65 coupled on the immobilization layer 10 may include irradiating the immobilization layer 10 containing functional groups protected with photolabile protecting groups with light, removing the photolabile protecting groups in a region irradiated with light to expose the functional groups, and coupling the probes 60 and 65 such as oligonucleotide probes, polypeptide probes, or peptide nucleic acid (PNA) probes onto the immobilization layer 10. In alternative exemplary embodiments, the biochip may be manufactured by in-situ synthesis of monomers using photolithography or coupling presynthesized oligomer probes onto the immobilization layer 10 by a spotting technique. However, the present general inventive concept is not limited thereto.

As described above, depending on the process environment, the probes 60 and 65 fabricated using the above-mentioned methods may contain the first probe 60 containing a desired number of monomers and the second probe 65 containing an undesired number of monomers. For example, if 25 monomers in a probe that constitute a base sequence for detecting specific bio-molecules are formed sequentially in-situ on the immobilization layer 10, a 25-th monomer or at least one of 1st through 24-th monomers may not be formed to form the second probe 65 containing an undesired number of monomers. In this way, the plurality of probes 60 and 65 include the first probe containing 25 monomers and the second probe 65 containing a different number of monomers than 25 monomers. However, the present general inventive concept is not limited thereto.

In exemplary embodiments, the second end (5'-terminus) of each of the first and second probes 60 and 65 may be phosphorylated before hybridization of a QC probe (the detection oligomer 1 illustrated in FIG. 4B) to the first and second probes 60 and 65. In exemplary embodiments, the phosphorylation may be performed using kinase such as T4 DNA kinase or chemical methods. However, the present general inventive concept is not limited thereto.

Subsequently, referring to FIG. 4B, the QC probe 1 (SEQ ID NO. 2) hybridizes to the first and second probes 60 and 65, which are coupled to the immobilization layer 10.

The first probe 60 is then connected to QC probe 1. More specifically, the second end (3'-terminus) of a second single strand of QC probe 1 (a base sequence in a stem 210 indicated by lowercase letters) is coupled with the second end (5'-terminus) of the first probe 60 by ligation or other chemical reactions. In exemplary embodiments, ligation may be carried out using T4 ligase, E. coil ligase, or Taq ligase as a ligand. However, the present general inventive concept is not limited thereto.

The second end of the first probe 60, having a desired number of monomers, is coupled with the second end of the second single strand in the stem 210 of the hairpin 200 by a ligase at a portion 70 where they meet with each other.

On the other hand, the second end of the second probe 65, having an undesired number of monomers, may not be coupled with the second end of a stem 210 of a hairpin 200 by a ligase at a portion 70 where they meet each other. That is, since there exists a space corresponding to a monomer between the second end of the second probe 65 and the second end of the stem 210 of the hairpin 200, the second probe 65 may not be coupled with QC probe 1. That is, as illustrated in a portion 75, the second end of the second probe 65 may not be coupled to the second end of the second single strand in the stem 210 of the hairpin 200.

Figure 4B:
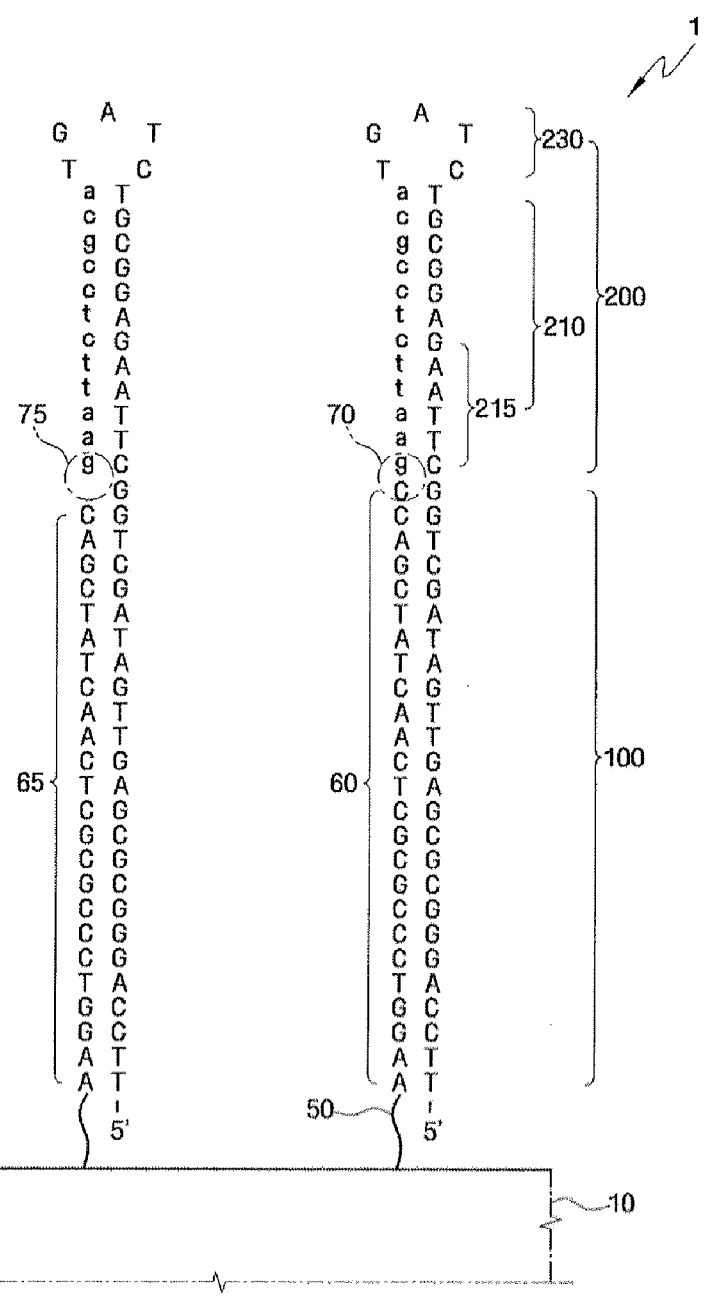

Further, although not illustrated in FIG. 4B, if the second probe 65 does not contain at least one of the 1st through 24-th monomers, a template 100 of QC probe 1 may be folded to cause steric hindrance which obstructs coupling between the second probe 65 and the QC probe 1 via the ligase.

In a method for controlling a quality of a biochip according to the current exemplary embodiment, a QC probe 1 is hybridized to the first probe 60 by the template 100 and connected to the first probe 60 by the hairpin 200. In this way, the QC probe 1 and the first probe 60 may be joined by a bimolecular reaction therebetween, thus improving an efficiency of a QC process. That is, the QC method according to the present general inventive concept may be performed more rapidly than a typical QC process, which uses a termolecular reaction that involves hybridizing a first template having a base sequence complementary to a base sequence of the first probe 60 to the first probe 60, hybridizing a second template tagged with a detection label to the first template, and coupling the second template with the first probe 60.

Figure 4C:
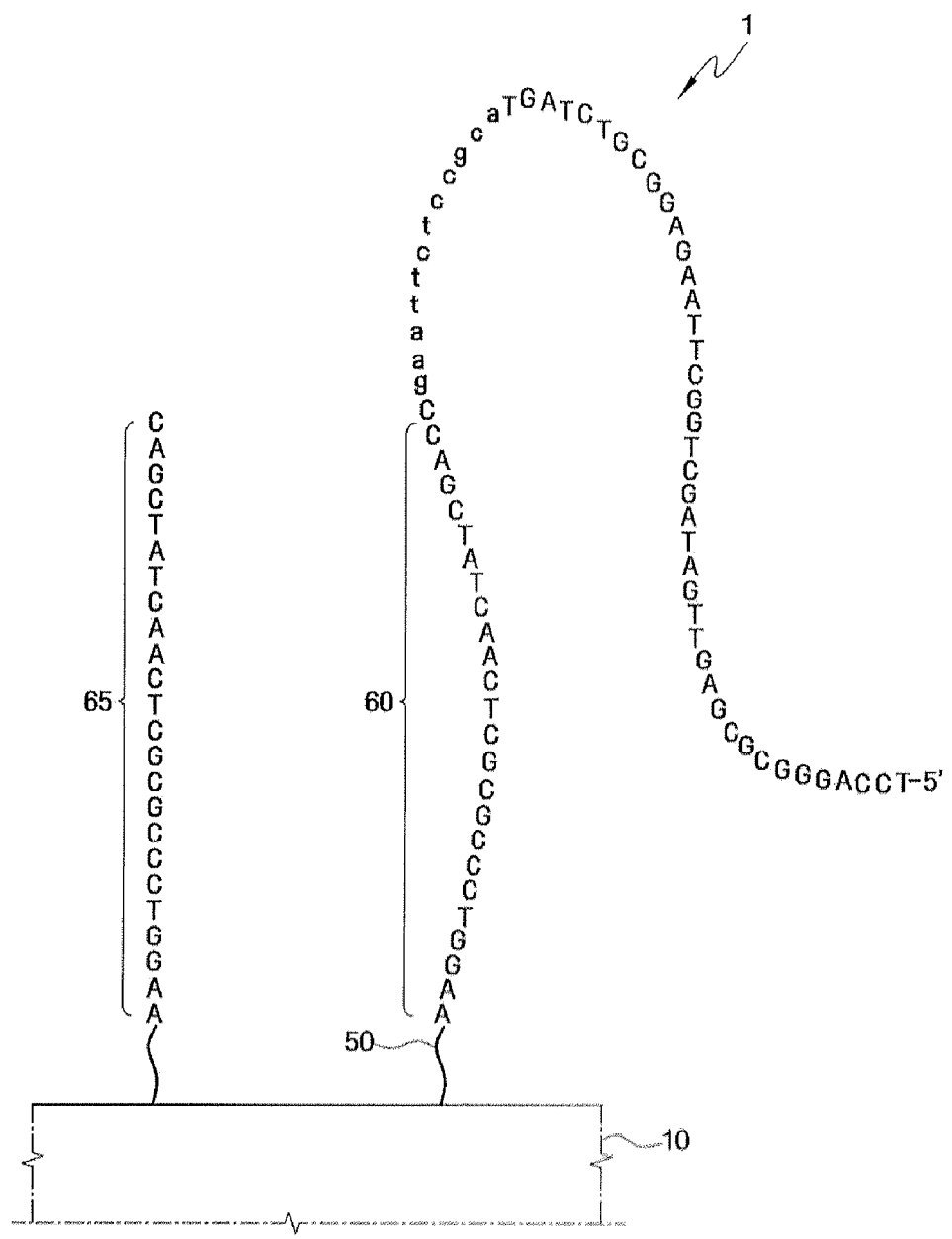

Referring to FIG. 4C, the resulting probe array is then washed in order to remove the hybridization coupling between each of the first and second probes 60 and 65 and the QC probe 1. In exemplary embodiments, removal of the hybridization coupling may be accomplished by adjusting a pH by adding alkali or by raising a temperature. However, the present general inventive concept is not limited thereto.

Following the wash step, the first probe 60 that was hybridized and coupled to the QC probe 1 connects with the QC probe 1 to form a single strand. The second probe 65 that was only hybridized to the QC probe 1 is converted into a single-stranded form without the QC probe 1 connected thereto.

Figure 4D:
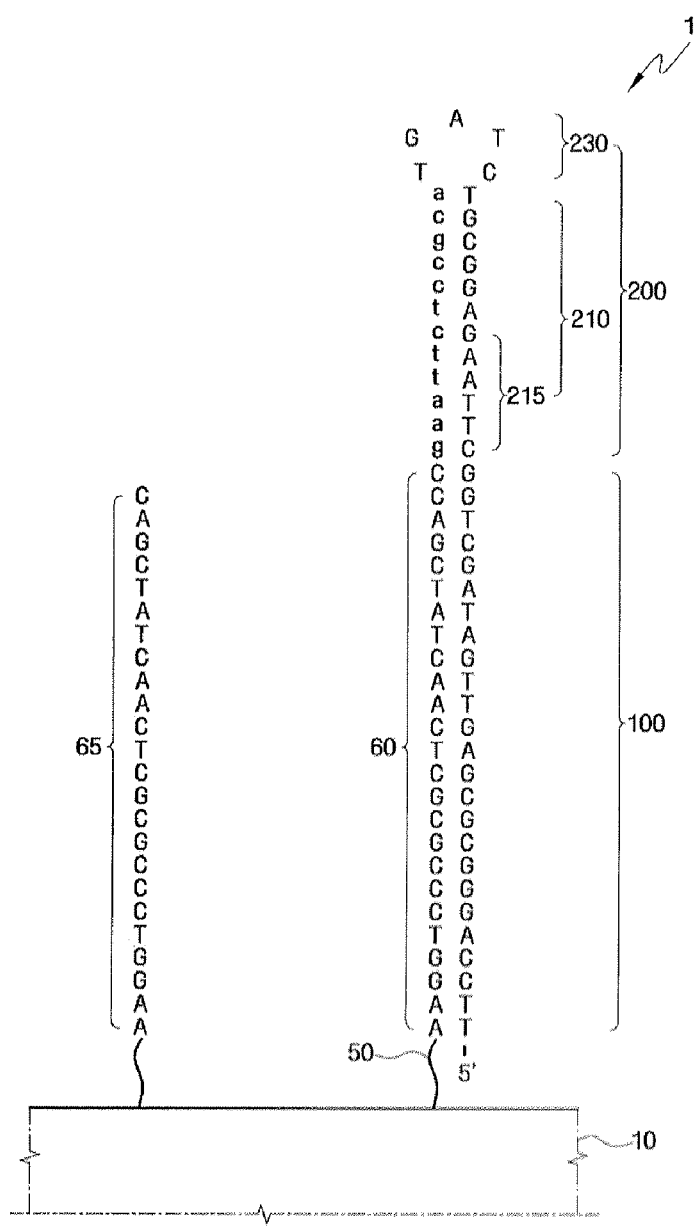

Referring to FIG. 4D, the first probe 60 hybridizes to the template 100 of the QC probe 1 to form a double strand. More specifically, the single strand formed by coupling the first probe with the QC probe 1 is converted into a double strand by hybridizing the first probe 60 and the template 100 of the QC probe 1, having complementary base sequences as well as the first and second single strands in the QC probe 1 possessing complementary base sequences. In exemplary embodiments, the conversion into a double strand may be accomplished by adjusting a pH or a temperature so that the complementary base sequences are again hybridized to each other.

Figure 4E:
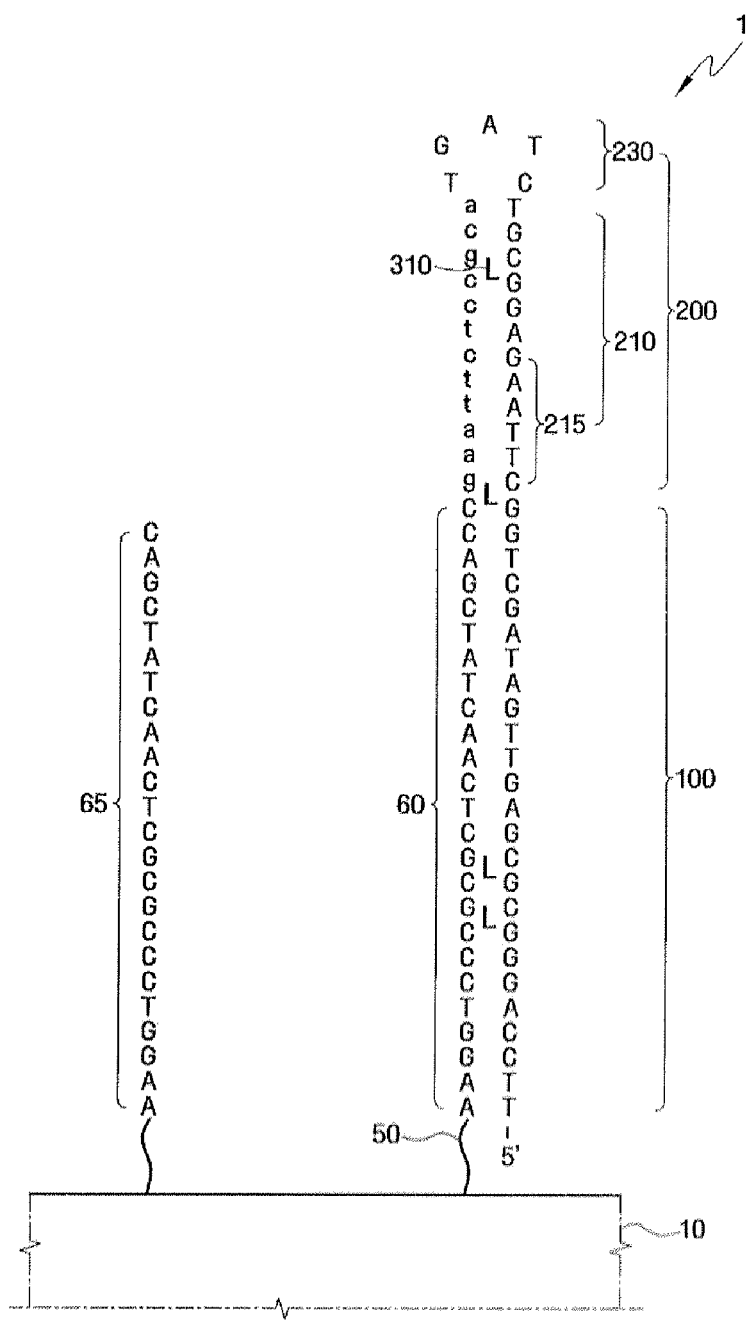

Referring to FIG. 4E, a label 310 is coupled to the double strand. In exemplary embodiments, the label 310 may be formed of a fluorescent or phosphorescent material that may be coupled to the double strand. In exemplary embodiments, the fluorescent or phosphorescent material include SYBR green I, SYBR green II, SYBR gold, Oxazole Yellow (OY), Thiazole Orange (TO), and Pico Green (PG). However, the present general inventive concept is not limited thereto. That is, the type, amount, and/or location of the label 310 may vary as desired.

An optical signal from the label 310 coupled to the first probe 60 is used to detect the first probe 60, containing a desired number of monomers, on the biochip. That is, it is possible to detect a ratio between the first probe 60 which contains the desired base sequence that can hybridize with bio-molecules on the biochip and the second probe 65 which does not contain the desired base sequence. Thus, a quality of the manufactured biochip may be measured.

Thereafter, in exemplary embodiments, the QC probe 1 may be decoupled from the first probe 60 by using nuclease or other chemical reactants. In exemplary embodiments, nuclease may be endonuclease or exonuclease. In an exemplary embodiment, a restriction endonuclease which is specific to a palindromic sequence 215 at one end of the stem 210 of the QC probe 1 may be used to decouple the QC probe 1 from the first probe 60. However, the present general inventive concept is not limited thereto.

The QC method according to the current exemplary embodiment may use nuclease for efficient decoupling between the QC probe 1 and the first probe 60 because the first QC probe 1 hybridizes to the first probe 60 to form the double strand. After measuring the quality of probes (such as the first probe 60 having the desired base sequence and the second probe having the undesired base sequence) that may detect target bio-molecules on the biochip, the above-mentioned process may be repeated in order to measure the quality for probes capable of detecting other target bio-molecules.

Figure 5:
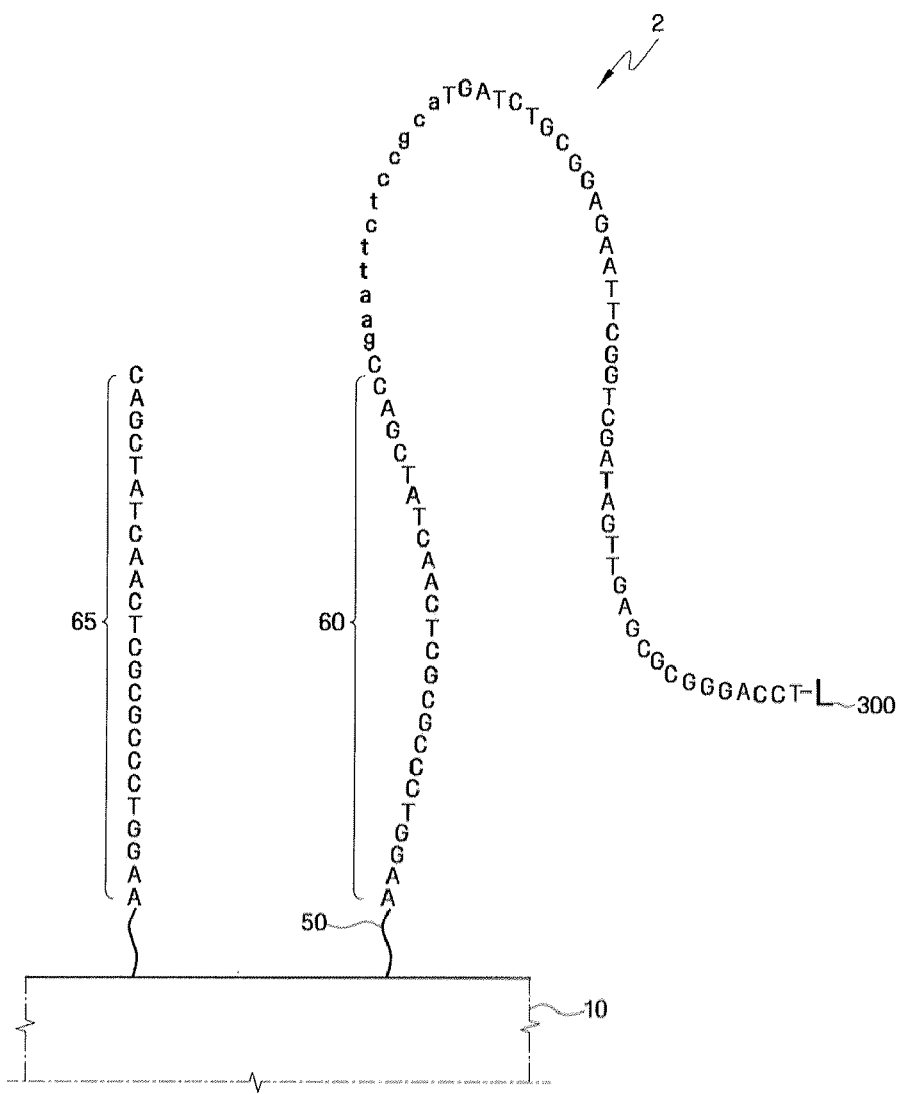
FIG. 5 is a diagram which illustrates a method for controlling the quality of a biochip according to another exemplary embodiment of the present general inventive concept.

FIG. 5 is a diagram which illustrates a method for controlling a quality of a biochip according to another exemplary embodiment of the present general inventive concept.

A QC probe used in the QC method according to the current exemplary embodiment may be made of the detection oligomer 2 illustrated in FIG. 2.

Referring to FIG. 5, the QC method according to the current exemplary embodiment differs from the QC method illustrated in FIGS. 4A through 4E in that the current exemplary embodiment uses a QC probe 2 (SEQ ID NO. 3) containing a label 300. According to the current exemplary embodiment, after removing the hybridization coupling between each of the first and second probes 60 and 65 and the QC probe 2, the first probe 60 containing a desired number of monomers may be detected.

More specifically, since the QC probe 2 contains the label 300, the QC method according to the current exemplary embodiment allows detection of the first probe 60 without the need for hybridizing the QC probe 2 again to the first probe 60 and coupling a separate label to the QC probe 2.

Although not illustrated in the drawings, according to another exemplary embodiment, a QC probe may contain a label coupled to a hairpin loop.

In alternative exemplary embodiments, a QC probe may be made of the detection oligomer 3 illustrated in FIG. 3. In this case, the quality of a biochip may be measured using the QC probe which may form a hair pin structure when the QC probe hybridizes with first and second probes.

In yet another exemplary embodiment, a QC probe may contain a label coupled to the first oligomer 103 and/or the second oligomer 203 in the detection oligomer 3.

Figure 6:
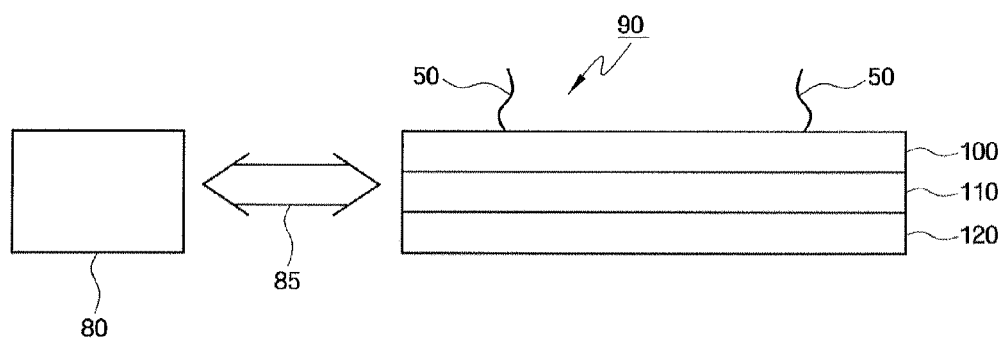
FIG. 6 is cross sectional view of a biochip attached to a controller according to an exemplary embodiment of the present general inventive concept.

FIG. 6 is cross sectional view of a biochip attached to a controller according to an exemplary embodiment of the present general inventive concept.

In an exemplary embodiment, the first and second probe 60 and 65 may be attached to at least a first layer 100 of the biochip 90. In alternative exemplary embodiments, the biochip 90 may further include a second and third layer 110 and 120 in order to provide electrical communication between biomolecules, probes, and/or oligomers attached to the first, second, or third layer 100, 110, and 120 with the controller 80. In an exemplary embodiment, the first layer 100 includes at least one linker 50 on which the first and second probes 60 and 65 may be affixed.

In exemplary embodiments, the controller 80 may be used to control, detect, and/or measure electrical signals generated by the biochip 90 via an electrical connection 85 therebetween. In other exemplary embodiments, the controller 80 may further include electrodes (not illustrated) on which the linkers 50 and the first and second probe 60 and 65 may be formed. In yet further exemplary embodiments, the controller 80 may be used a power supply to provide electrical signals to the biochip 90.

Although a few exemplary embodiments of the present general inventive concept have been particularly shown and described with reference to exemplary embodiments thereof, it will be appreciated by those of ordinary skill in the art that various changes in form and details may be made in these exemplary embodiments without departing from the principles and spirit and scope of the general inventive concept, the scope of which is defined by the following claims. It is therefore desired that the present embodiments be considered in all respects as illustrative and not restrictive, reference being made to the appended claims rather than the foregoing description to indicate the scope of the invention.

What is claimed is:

1. A method of assessing biochip quality, the method comprising:
   providing a biochip comprising at least first full length polynucleotide probes and second truncated polynucleotide probes, each having first ends that are coupled to an immobilization layer, the first full length polynucleotide probes having a different number of nucleotide monomers than the second truncated polynucleotide probes;
   hybridizing Quality Control (QC) probes to the first full length polynucleotide probes and second truncated polynucleotide probes, each QC probe comprising:
      a template portion having a nucleotide sequence complementary to a nucleotide sequence of the first full length polynucleotide probes and second truncated polynucleotide probes; and
      a hairpin connected to a first end of the template portion;
   exposing the biochip to conditions suitable for ligation of polynucleotides;
   washing the biochip to de-hybridize the QC probes from the first full length polynucleotide probes and second truncated polynucleotide probes, thereby removing unligated QC probes;
   detecting a ratio of the amount of the first full length polynucleotide probes that are ligated to the QC probes to the amount of the second truncated polynucleotide probes that are ligated to the QC probes to assess biochip quality, wherein the quality of the biochip is a measure of the relative amounts of first full length polynucleotide probes and second truncated polynucleotide probes.

2. The method of claim 1, further comprising:
   phosphorylating second ends of the first full length polynucleotide probes and second truncated polynucleotide probes before the hybridizing.

3. The method of claim 1, wherein:
   the hairpin comprises a stem comprising complementary first and second single strands and a loop, the first single strand having a first end that is coupled with the loop and a second end that is coupled with a first end of the template portion, and the second single strand having a second end that is coupled with the loop and a first end that is ligated to the second end of the first full length polynucleotide probe during the exposing the biochip to conditions suitable for ligation.

4. The method of claim 1, wherein:
   the hairpin comprises a stem having complementary first and second single strands and a loop; and
   after the hybridizing, first ends of the second strands of the QC probes hybridized to the second truncate polynucleotide probes are spaced apart from the second ends of the second truncated polynucleotide probes.

5. The method of claim 1, further comprising:
   after the washing, re-hybridizing the full length polynucleotide probes to the template portion of the ligated QC probes to form double stranded structures;
   intercalating a label into the double stranded structures; and
   detecting the label.

6. The method of claim 1, wherein:
   the QC probes each further comprise a label coupled to one of the template portion and the hairpin; and
   the method further comprises detecting the label after the washing.

7. The method of claim 5, further comprising removing the ligated QC probes after the detecting of the label.

8. The method of claim 7, wherein:
   the hairpins each comprise a stem comprising complementary first and second single strands and a loop, the first single strand having a first end coupled with the loop, a second end coupled with a first end of the template portion, and a sequence specific to a nuclease, the second single strand having a first end coupled with the loop and a sequence specific to a nuclease; and
   removing of the ligated QC probes is performed using a nuclease that binds to the specific sequences.

9. A method of assessing biochip quality, the method comprising:
providing a biochip comprising:
an immobilization layer; and
at least first full length polynucleotide probes and second truncated polynucleotide probes, each having 3' ends that are coupled to the immobilization layer, the first full length polynucleotide probes having a different number of nucleotide monomers than the second truncated polynucleotide probes;
hybridizing Quality Control (QC) probes to the first full length polynucleotide probe and second truncated polynucleotide probe, each QC probe comprising a template portion having a nucleotide sequence complementary to the entire first full length polynucleotide probe; and
exposing the biochip to conditions suitable for ligation of 3' ends of the QC probes to 5' ends of the first full length polynucleotide probe and second truncated polynucleotide probe;
washing the biochip to de-hybridize the QC probes from the first full length polynucleotide probes and second truncated polynucleotide probes, thereby removing unligated QC probes;
detecting a ratio of the first amount of the first full length polynucleotide probes that are ligated with the QC probes to the amount of the second truncated polynucleotide probes that are ligated to the QC probes to assess the quality of the biochip, wherein the quality of the biochip is a measure of the relative amounts of the first full length and second truncated polynucleotide probes.

10. The method of claim 9, wherein detecting comprises:
annealing the ligated QC probes and the first full length polynucleotide probes to produce double-stranded structures; and
intercalating a label into the double-stranded structures.

11. The method of claim 9, further comprising completely removing the ligated QC probes from the biochip.

* * * * *